United States Patent
Leone et al.

[19]

[11] Patent Number: 5,811,814
[45] Date of Patent: Sep. 22, 1998

[54] RADIATION MEASURING CATHETER APPARATUS AND METHOD

[75] Inventors: James E. Leone; Stephen M. Rowland, both of Miami, Fla.

[73] Assignee: Cordis Corporation, Miami Lakes, Fla.

[21] Appl. No.: 599,824

[22] Filed: Feb. 12, 1996

[51] Int. Cl.$^6$ .......................... G01T 1/161; G01T 1/202; A61B 6/00
[52] U.S. Cl. .......................... 250/368; 250/369; 128/659
[58] Field of Search .......................... 250/368, 369; 128/656, 657, 658, 659

[56] References Cited

U.S. PATENT DOCUMENTS

| | | |
|---|---|---|
| 3,427,454 | 2/1969 | Webb . |
| 4,015,592 | 4/1977 | Bradley-Moore . |
| 4,595,014 | 6/1986 | Barrett et al. .......................... 128/659 X |
| 5,012,809 | 5/1991 | Shulze . |
| 5,023,123 | 6/1991 | Katz et al. . |
| 5,166,073 | 11/1992 | Lefkowitz et al. .................. 128/659 X |
| 5,229,613 | 7/1993 | Pandelisev et al. .................... 250/368 |
| 5,263,963 | 11/1993 | Garrison et al. . |
| 5,306,261 | 4/1994 | Alliger et al. .......................... 128/657 X |
| 5,325,855 | 7/1994 | Daghighian et al. . |
| 5,326,531 | 7/1994 | Hahn et al. . |
| 5,331,961 | 7/1994 | Inaba et al. .......................... 250/368 X |
| 5,424,546 | 6/1995 | Okada et al. .......................... 250/368 X |

OTHER PUBLICATIONS

One page setting forth two graphs entitled "Absorbtion Efficiency of NaI(tl)" and Gamma and X–ray Transmission through Bicron Detector Windows compiled from NBS Circular 583 and supplement to NBS Circular 583, publication date of NBS Circular 583—1956, publication date of NBS Circular supplement—unknown.

One page setting forth a table entitled "Table of Physical Constants of Scintillators", undated.

One page specification sheet for Toray Plastic Optical Fiber, undated.

Three page brochure entitled "Hamamatsu Technical Data— Metal Package Photomultiplier Tube R5600 U Series," publication date—Jan. 1994.

Three pages from textbook entitled "Introductory to Nuclear Physics", pp. 194–197 and 208–209, publication date—unknown.

Two page specification sheet for Tennelec/Nucleus PCA–P Spectroscopy System, undated.

*Primary Examiner*—Edward J. Glick
*Attorney, Agent, or Firm*—Watts, Hoffmann, Fisher & Heinke Co. L.P.A.

[57] ABSTRACT

An apparatus for measuring radiation at a region of interest inside a body is disclosed. The apparatus comprises a fiber optic equipped-catheter having a distal portion adapted to be inserted in a blood vessel. The apparatus further includes a luminescent scintillation material coupled to the fiber optic light pipe. The scintillation material is disposed in a distal portion of a lumen of the catheter and generates pulses of electromagnetic radiation in response to excitation by radiation rays. The apparatus further includes an index matching material disposed between the scintillation crystal and the fiber optic light pipe facilitating transmission of the pulses of electromagnetic radiation produced by the scintillation material to the fiber optic light pipe. A measuring assembly is coupled to the fiber optic light pipe to convert the pulses of radiation traversing the fiber optic light pipe to a measure of radiation in the region of interest. A method of measuring radiation using the radiation measuring apparatus of the present invention is also disclosed. The steps of the method comprise: providing a catheter having a fiber optic light pipe coupled to a scintillation material supported by a distal portion of the catheter; inserting the distal portion of the catheter through an opening in the body; maneuvering the catheter to position the distal portion of the catheter within the region of interest; and converting the pulses of electromagnetic radiation transmitted along the fiber optic light pipe into a measure of radiation.

14 Claims, 2 Drawing Sheets

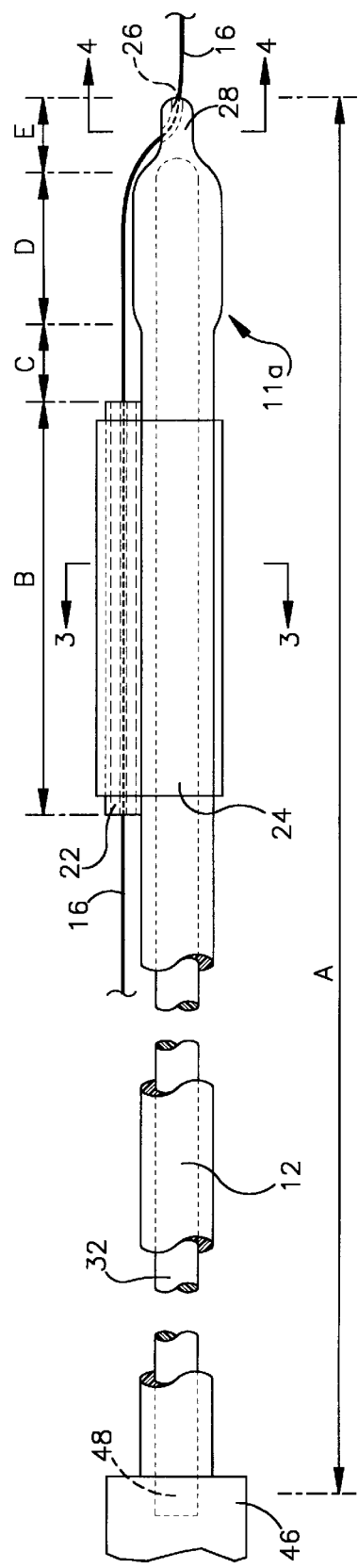
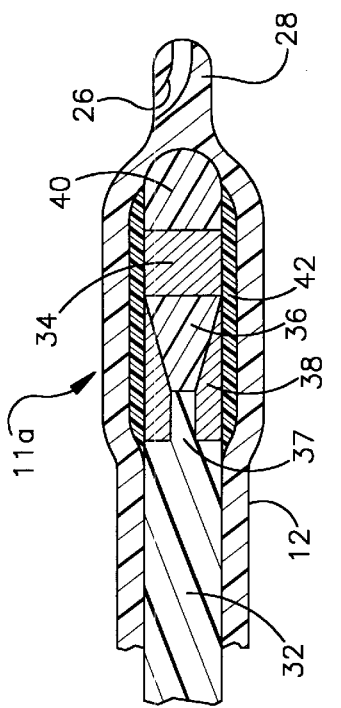
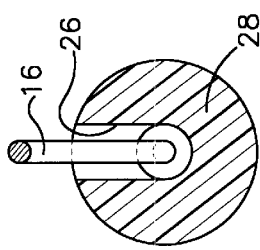
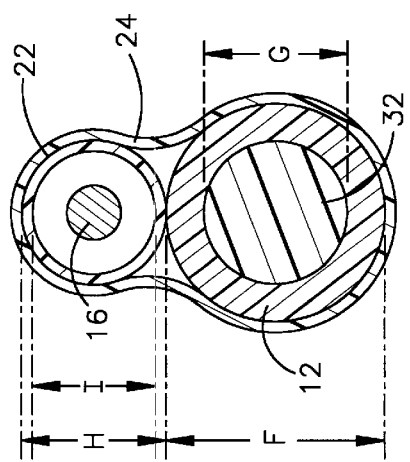

RADIATION MEASURING CATHETER APPARATUS AND METHOD

TECHNICAL FIELD

This invention pertains to an apparatus and method for measuring radiation levels in a region of interest in a body of a subject and, more particularly, to a radiation measurement apparatus including a fiber optic-equipped catheter having a radiation sensitive scintillation material disposed within a distal portion of the catheter, the distal portion of the catheter adapted to be inserted and maneuvered through a blood vessel to the region of interest.

BACKGROUND ART

"Tagged drugs" are widely used in nuclear medicine to locate infected or damaged portions of blood vessels and internal body organs, for example, the liver or kidneys. A tagged drug includes radioactive isotopes attached to carrier molecules. The radioactive isotopes in tagged drugs generally have a short half life (6 hours is typical) and emit low energy gamma rays and beta rays. When a tagged drug is injected into a blood vessel, the carrier molecules attach themselves to cells in the in bloodstream. The carrier molecules of certain tagged drugs attach themselves to red blood cells, while other tagged drugs have carrier molecules which attach to white blood cells.

Depending on the medical condition to be diagnosed, a red or white blood cell attaching tagged drug is chosen. For example, if the diagnoses involves locating an infected portion of a blood vessel, a white blood cell attaching tagged drug is used since white blood cells will congregate at the site of the infection to fight the infection. Therefore, a greater concentration of tagged white blood cells will be found at the infected portion of the blood vessel. This results in a higher level of gamma and beta ray radiation at the infection site. As such, the infection site may be pinpointed with a suitable radiation measurement device.

An exemplary use of a red blood cell attaching tagged drug involves locating the position of an aneurism in a blood vessel wall. An aneurism is a weakening of a portion of a blood vessel wall. In the aneurism area, the wall may have a small a hole that allows blood to escape the vessel or the wall may be stretched so thin that blood cells are able to seep through the wall.

As the tagged red blood cells flow through the bloodstream, some of the tagged cells will seep or leak out of the blood vessel in the aneurism area and accumulate outside the vessel wall. A higher level of gamma and beta ray radiation will be detected at the aneurism location due to the accumulation of radioactive isotopes outside the weakened blood vessel wall portion.

Tagged drugs can also be used to located the position of a damaged or diseased portion of an internal organ. An appropriate tagged drugged is injected "upstream" of the organ and, as described above, a higher concentration of tagged blood cells will be found at the situs of the disease or injury.

Conventionally, the level of radiation emitted by the tagged drugs in the body is visualized by a physician or nuclear medicine technician using a fluoroscopy device, typically a gamma camera. As its name implies, the gamma camera detects gamma ray radiation and provides a visual "map" of the levels of radiation emitted from an area of the body viewed on the viewing screen. The gamma camera is positioned externally to the body and includes a large single scintillation crystal or a multiplicity of smaller scintillation crystals. When a photon associated with a gamma, beta ray impacts and is absorbed by a scintillation crystal, the crystal scintillates and emits a light pulse at the location of impact.

The gamma camera also includes one or more photodetector tubes, associated circuitry and a viewing screen which converts the pulses of light emitted by the scintillation crystal into a radiation level "map" of the area of the body the gamma camera is positioned adjacent to. The image represented on the viewing screen represents levels of radiation over the area monitored. The darker an area on the viewing screen, the greater the level of measured radiation. The darkest regions on the viewing screen indicate high levels of radiation and are commonly called "hot spots." A hot spot represents a concentration of tagged blood cells and is found at the location of the diseased or damaged blood vessel.

While the gamma camera, used in combination with tagged drugs, has proven to be a useful medical diagnostic tool, its ability to precisely locate a position of damaged or diseased portions of a blood vessel or internal organ is compromised by virtue of the gamma camera being external to the subject's body and, therefore, a significant distance from the source of the radiation in the body. For health reasons, the quantity and strength of the radioactive isotopes incorporated into a dosage of a tagged drug must be minimized to avoid the deleterious effects of radiation to the patient. The emitted radiation from the tagged drug isotopes are relatively weak (normally on the order of 100's of kilo electron volts (keVs)).

All other things being equal, the closer to the source of radiation a measuring device is, the more accurate the measurement of that radiation. The strength of the radiation emitted ("signal") by a source of radiation decreases proportionately with the square of the distance from the source. Therefore, the closer to the source of radiation a radiation measuring device is, the stronger the "signal" it will receive and the more precisely the location of the radiation can be pinpointed. With the gamma camera external to the body, the relatively weak radiation generated by the isotopes will often be insufficient to allow the physician or nuclear medicine technologist to accurately pinpoint the location of the problem area.

The present invention effectively moves the radiation measurement device adjacent to the source of radiation, thereby facilitating accurate and efficient measurement of radiation levels and permitting precise determination of the damaged or diseased area of the blood vessel or internal organ.

SUMMARY OF THE INVENTION

The apparatus of the present invention is adapted to accurately measure radiation at a region of interest inside a body. The apparatus comprises a catheter adapted to be inserted into a blood vessel, a length of the catheter is sufficient to extend to the region of interest while a proximal end of the catheter remains outside the body.

The apparatus includes a luminescent scintillation material disposed in a distal portion of a lumen of the catheter. When a photon associated with an alpha, beta, gamma or X-ray strikes and is absorbed by the scintillation material, the scintillation material luminesces and emits a pulse of electromagnetic radiation in the visible spectrum, i.e., a pulse of light. A fiber optic light pipe is also disposed in the lumen of the catheter proximal to the scintillation material. An index matching material optically couples the scintillation material to a distal end of a fiber optic light pipe. The generated pulses of light are received by and transmitted along the fiber optic light pipe.

The portion of the fiber optic light pipe extending beyond a proximal end of the catheter is coupled to a photomultiplier tube. The generated pulses of light traversing the fiber optic light pipe are received by the photomultiplier tube and converted to electric signals. The signals are input to a signal processor analyzer which converts the photomultiplier signals into a relative measure of radiation. The signal processor analyzer in turn is coupled to an output display which permits a physician or nuclear medicine technologist to continuously monitor the radiation level at the distal end of the catheter as the distal end is advanced into and through the region of interest.

The scintillation material is preferably cylindrically shaped to snugly fit within the cylindrical catheter lumen. To make the apparatus directionally sensitive, radiation blocking material is disposed in the catheter lumen adjacent distal and proximal end walls of the scintillation material. The radiation blocking material blocks photons emitted by sources of radiation in front of or behind the scintillation material, that is, sources of radiation in axial alignment with a major or longitudinal axis of the scintillation material for the most part will not be detected or measured. Only photons traveling along paths that intersect the side wall of the scintillation material will impact the scintillation material and be detected. Thus, the apparatus detects sources of radiation radially outwardly of the scintillation material side wall and blocks detection of sources of radiation axially aligned with the scintillation material end walls.

The scintillation material preferably comprises a scintillation crystal. If the apparatus is to be used to measure gamma radiation, a scintillation crystal comprising Cesium Iodide doped with Thallium (CsI(Tl)) is preferable. A CsI (Tl) scintillation crystal is non-hygroscopic, has a relatively high absorption efficiency and when energized produces easily detectable pulses of light. The absorption efficiency of a scintillation material is the efficiency with which the crystal absorbs gamma energy and converts the energy to scintillations of light. Alternately, a scintillation crystal comprising Sodium Iodide doped with Thallium (NaI(Tl)) may be employed to measure gamma radiation. A plastic scintillation phosphor may be utilized in the apparatus in lieu of a scintillation crystal. Such a plastic scintillation material is best suited to the measurement of beta radiation.

A method of measuring radiation in a region of interest inside a body using the radiation measuring apparatus of the present invention is also disclosed. The steps of the method comprise: providing a radiation measuring apparatus including a catheter with a fiber optic light pipe extending through a lumen of the catheter, the fiber optic light pipe being optically coupled to a scintillation material disposed in the catheter lumen in a distal portion of the catheter; inserting the distal portion of the catheter through an opening in the body; maneuvering the catheter to position the distal portion adjacent a region of interest, the scintillation material generating pulses of electromagnetic radiation upon being impacted by and absorbing photons associated with radioactivity, the generated pulses of electromagnetic radiation traversing the fiber optic light pipe; sensing the pulses of electromagnetic radiation traversing the fiber optic light pipe; and converting the sensed bursts of electromagnetic radiation into a measure of radiation at the region of interest. The step of converting the sensed pulses of electromagnetic radiation into a measure of radiation includes the substep of converting the pulses of electromagnetic radiation to electric pulses.

Additional features of the invention will become apparent and a fuller understanding obtained by reading the following detailed description made in connection with the accompanying drawings.

BRIEF DESCRIPTION OF THE DRAWINGS

FIG. 2 is an enlarged fragmentary front elevation view of the radiation measurement apparatus of FIG. 1;

FIG. 3 is a section view of the radiation measurement apparatus of FIG. 1 as seen from the plane indicated by line 3—3 in FIG. 2;

FIG. 4 is a section view of the radiation measurement apparatus of FIG. 1 as seen from the plane indicated by line 4—4 in FIG. 2; and FIG. 5 is an enlarged longitudinal sectional view of a distal portion of the radiation measurement apparatus of FIG. 1.

DETAILED DESCRIPTION OF THE INVENTION

Figure 1:
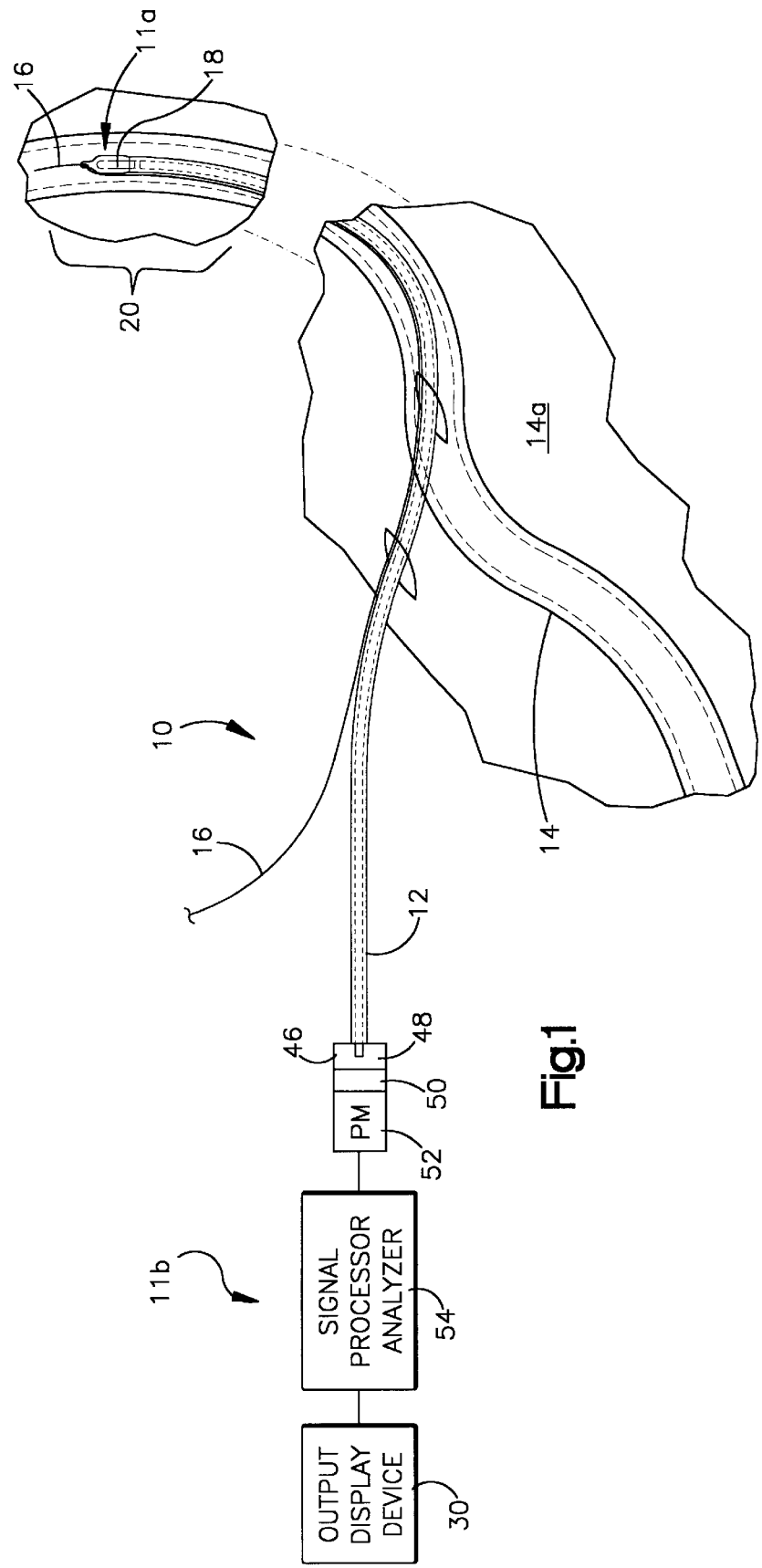
FIG. 1 is a schematic representation of a radiation measurement apparatus of the present invention in use, a radiation detecting portion of a catheter extends into a patient's blood vessel while the radiation measurement portion remains outside the patient's body.

Turning to the drawings, FIG. 1 illustrates a radiation measurement apparatus of the present invention, shown generally at 10, in use. The apparatus 10 includes a radiation detecting assembly 11a and a radiation measurement assembly 11b (best seen in FIG. 5). The radiation detecting assembly 11a is disposed in a lumen of a catheter 12 and bulges a wall defining the lumen slightly outwardly (as can best be seen in FIGS. 2 and 5). A portion of the catheter 12 extends into a subject's blood vessel 14 through an opening in the subject's skin 14a.

A guidewire 16 is used to guide a distal portion 18 of the catheter 12, including the radiation detecting assembly 11a, to a region of interest 20 of the blood vessel 14. (Only a portion of the total guidewire 16 is shown in the Figures.) The region of interest 20 is a portion of the blood vessel 14 along which a level of radiation is desired to be measured. The distal portion 18 of the catheter 12 slides along the guidewire 16 to the region of interest 20 of the blood vessel 14. The guidewire 16 is comprised of a tightly wound stainless steel coil coated with TEFLON® coating or other low coefficient of friction material. The guidewire 16 has an outer diameter of approximately 0.5 mm to 1.0 mm. (0.02 in. to 0.04 in.).

The guidewire 16 is inserted using a guidewire insertion catheter (not shown). When the guidewire is properly positioned to extend somewhat beyond the region of interest 14b of the blood vessel 14, the guidewire insertion catheter is withdrawn, leaving the guidewire 16 in place. The distal portion 18 of the catheter 12 slides along the guidewire 16.

As can best be seen in FIGS. 2 and 3, the guidewire 16 is threaded through a section of tube 22 which is affixed to the catheter by a length of plastic heat shrink tubing 24. Heat is applied to the tubing 24 to snugly secure the section of tube 22 to the catheter 12. The guidewire 16 is further threaded through an angled aperture 26 (best seen in FIG. 5) in a nipple portion 28 of the catheter 12. The nipple portion 28 is located at an end of the catheter distal portion 18. The angled aperture 26 is rounded and extends from a side wall of the nipple portion 28 to a distal end of the nipple portion 28.

As the distal portion 18 of the catheter 12 is advanced along the guidewire 16 through the blood vessel 14, the apparatus 10 provides a continuous measure of radiation intensity detected by the radiation detection assembly 11a. The detected radiation is converted to a relative measure of radiation by the radiation measurement assembly 11b which is outside the subject's body. The radiation measurement assembly 11b includes an output display device or monitor 30. The monitor 30 permits a physician or nuclear medical technologist to continuously monitor changes in radiation level as the distal portion 18 of the catheter 12 is advanced through the blood vessel 14.

Additionally, the advancement of the distal portion 18 of the catheter 12 may be viewed on a fluoroscopy screen. A "hot spot" of high radiation produced by photons emitted by the radioactive isotopes of a tagged drug is indicative of a diseased or damaged portion of the blood vessel 14. When such a "hot spot" is encountered, the location and length of the "hot spot" area is accurately noted and, upon removal of the catheter 12, appropriate treatment may be instituted.

Because the detection of radiation is taken in close proximity to the source or sources of the radiation in the body, the measurement of radiation intensity or level by the apparatus 10 is very accurate.

The radiation detecting assembly 11a and the radiation measuring assembly 11b are optically coupled by a fiber optic light pipe 32. The fiber optic light pipe 32 is preferably comprised of plastic for greater flexibility, although it should be appreciated that a quartz fiber optic light pipe could also be utilized. The fiber optic light pipe 32 has an outside diameter of between 0.25 mm. and 0.75 mm. (0.010 in. to 0.030 in.). A suitable quartz fiber optic light pipe may be purchased from Ceramoptec of Enfield, Conn. A suitable PMMA plastic fiber optic light pipe may be purchased from Toray of Japan.

As can best be seen in FIG. 5, the radiation detecting assembly 11a is disposed within a distal section of the lumen of the catheter 12. The radiation detecting assembly 11a includes a scintillation material 34, an index matching material 36, a pair of radiation blocking members 38, 40 and a section of plastic heat shrink tubing 42 which overlies the other components of the radiation detecting assembly 11a.

The scintillation material 34 is cylindrical in shape sized to snugly fit in the lumen of the catheter 12. The scintillation material 34 is approximately 1 mm. (0.04 in.) in length and approximately 1 mm. to 2 mm. (0.04 in. to 0.08 in.) in diameter. When the scintillation material 34 is struck by an alpha, beta, gamma, or X-ray, that radiation is absorbed by the scintillation material, the scintillation material scintillates or luminesces, that is, the material generates a pulse of electromagnetic radiation. If the generated pulse of electromagnetic radiation has a wavelength in the visible spectrum, the pulse of electromagnetic radiation is a pulse of visible light. Not all radiation striking the scintillation material 34 is absorbed by the material and results in the generation of a pulse of electromagnetic radiation.

The "absorption efficiency" of the scintillation material 34 is a measure of the percent of energy absorbed by a scintillation material of a given thickness when a parallel beam of radiation is directed at the scintillation material. The scintillation material 34 for the apparatus 10 preferably is a scintillation crystal comprised of Cesium Iodide doped with Thallium (CsI(Tl)). A CsI(Tl) scintillation crystal is characterized by a good absorption efficiency with respect to gamma rays. A CsI(Tl) scintillation crystal 1 mm. (0.04 in.) thick would absorb approximately 35% of the energy of a 100 keV gamma or x-ray normally incident to the crystal. Additionally, a CsI(Tl) scintillation crystal generates pulses of electromagnetic radiation having a wavelength of approximately 580 nanometers (nm.), such pulses constitute easily detectable pulses of visible light. Further, a CsI(Tl) scintillation crystal is non-hygroscopic, that is, the crystal does not react with water. A CsI(Tl) scintillation crystal is commercially available from NE Technology Ltd. of Edinburgh, Scotland. NE Technology Ltd. is a division of Bicron of Newbury, Ohio.

Alternately, the scintillation material 34 may be comprised of a Sodium Iodide crystal doped with Thallium (NaI(Tl)) which also is suitable for detecting gamma rays and produces pulses of light having a wavelength of approximately 413 nm. If beta radiation is being detected, a plastic phosphor scintillation material is preferable. An appropriate phosphor scintillation material is available from NE Technology of Edinburgh, Scotland, part number NE102A.

The index matching material 36 optically couples the scintillation material 34 to a necked down distal portion 37 the fiber optic light pipe 32. The necked down distal portion 37 has an outer diameter of approximately 0.055 mm. (0.0022 in.). The index matching material 36 facilitates the transfer of light pulses generated by the scintillation material 34 to the fiber optic light pipe 32 and minimizes reflection of light pulses away from the fiber optic light pipe. The index matching material is preferably a flexible optical gel or grease. An appropriate flexible optical grease is available from Bicron of Newbury, Ohio, part number BC630.

The first radiation blocking member 38 is comprised of a ring of radiation blocking metal having a length of about 2 mm. (0.08 in.). Platinum and iridium are suitable materials. The member 38 overlies the necked down distal portion 37 of the optical fiber light pipe 32 and the index matching material 36 and abuts a proximal end wall of the scintillation material 34. The second radiation blocking member 40 is cylindrically shaped polyurethane doped with bismuth trioxide ($BiO_3$) (approximately 60% by volume). The blocking member has a length of about 2 mm. (0.08 in.). The first and second radiation blocking members 38, 40 function to make the radiation detection of the apparatus 10 directionally sensitive.

The radiation blocking members 38, 40 block most of the rays emitted by sources of radiation in front of or behind the scintillation material 34, that is, sources of radiation in axial alignment with a major or longitudinal axis of the scintillation material. Only photons traveling along paths that intersect a side wall of the scintillation material 34 will impact the scintillation material and cause a pulse of light to be generated. Thus, the apparatus 10 detects and measures sources of radiation radially outwardly of the scintillation material side wall and blocks detection of sources of radiation axially aligned with the scintillation material end walls.

The plastic heat shrink tubing 42 overlies the radiation detecting components 11a and is heated to shrink thereby securing the components into a unitary structure that the catheter 12 can be "pulled over" during assembly of the apparatus 12. The tubing 42 also prevents the index matching material 36 from leaking along the lumen of the catheter 12. The tubing 42 extends from the optical fiber light pipe 32 proximal to the necked down portion 37 to about half way along the length of the second radiation blocking member 40.

A coating comprising titanium oxide ($TiO_2$) is applied to the tubing and outer radial surfaces of the scintillation material 34 contacted by the tubing. The $TiO_2$ is highly light reflective and functions to integrate or colluminate the pulses of light generated by the scintillation material 34 into the index matching material 36 and ultimately the distal portion 44 of the optical fiber light pipe 32. The $TiO_2$ permits the photons to pass through to the scintillation material 34 with no significant absorption or attenuation. Alternately, instead of applying the $TiO_2$ coating to the outer surface of the radiation detecting components, the tubing 42 may be doped with $TiO_2$ particles.

The catheter 12 is comprised of soft nylon or polyurethane material which is doped with 40% $TiO_2$ by volume. The $TiO_2$ doping provides for light reflectivity to minimize losses of pulses of light generated by a scintillation material 34 and transmitted through the optical fiber light pipe 32. The $TiO_2$ dopant particles function as a barrier to keep light from outside the catheter 12 from being transmitted through the catheter wall into the lumen and minimizes loss of pulses of light traveling along the optical fiber light pipe 32. The doped catheter wall provides a relatively non-absorptive, non-attenuating shield for the gamma and beta rays emitted by radioactive isotopes to penetrate and excludes water and other ambient substances which would adversely affect the radiation detecting assembly components disposed within the catheter lumen.

Approximate dimensions of the catheter 12 and the tube section 20, labeled with reference letters A through I in FIGS. 2 and 3 are as follows:

| Label | Description | Length or Diameter |
|---|---|---|
| A | Catheter overall length | 160 cm. (63.0 in.) |
| B | Tube section | 15 cm. (5.9 in.) |
| C | Catheter section length between tube section and radiation detecting assembly | 2.5 cm. (1.0 in.) |
| D | Catheter radiation detecting section length | 5 mm. (0.20 in.) |
| E | Catheter nipple section length | 5 mm. (0.20 in.) |
| F | Catheter outside diameter | 1 mm. (0.04 in.) |
| G | Catheter inside diameter | 0.5 mm. (0.02 in.) |
| H | Tube section outside diameter | 0.55 mm. (0.024 in.) |
| I | Tube section inside diameter | 0.5 mm. (0.02 in.) |

A portion of the catheter 12 overlying the radiation detecting assembly 11a is bulged or stretched radially outwardly as can be seen in FIGS. 2 and 5. As noted above the scintillation material 34 has an outside diameter of approximately 1 mm. (0.004 in.). Thus, lumen of the catheter 12 must stretch radially outwardly from its normal diameter of approximately 0.5 mm. (0.02 in.) to accommodate the scintillation material 34 when the catheter 12 is "pulled over" the radiation detecting assembly.

The pulses of light generated by the scintillation material 34 are transmitted though the index matching material 36 and into the distal portion 37 of the fiber optic light pipe 32. The generated pulses of light traverse the fiber optic light pipe 32. A proximal portion 48 of the fiber optic light pipe 32 is optically coupled to the radiation measuring assembly 11b, which convert the pulses of light into electric signals which provide a relative measure of the intensity of the radiation detected by the radiation detecting assembly 11a.

The radiation measuring assembly 1ib includes an optical fiber adaptor (FC type) 46, a socket assembly 50 and a photomultiplier tube 52. These components function to convert the pulses of light transmitted along the fiber optic light pipe 32 into electric signals. A signal processor analyzer 54 is coupled to the photomultiplier tube 52 and converts the electrical signals output by the photomultiplier tube 52 into a measure of radiation. Finally, as noted previously, the display monitor 30 is coupled to the signal processor analyzer 54 and provides a visual display of the measure of radiation.

An appropriate optical fiber adaptor 46 is sold by Hammamatsu Phototronics K.K., part number E5775. As can be seen in FIG. 1, the proximal end portion 48 of the fiber optic light pipe 32 extends into an end of the adaptor 46. A D-type socket assembly 50 is received in an opposite end of the adaptor 46. A suitable D-type socket assembly, also sold by Hammamatsu, is part number E5780. The D-type socket assembly includes sockets adapted to receive the terminal pins (not shown) of a metal can type photomultiplier tube 52. A suitable photomultiplier tube is Hammamatsu's part number R5600.

The photomultiplier tube 52 converts and amplifies the pulses of light emanating from the proximal end 48 of the fiber optic light pipe into electrical signals. The output signals of the photomultiplier tube 52 are coupled to a signal processor analyzer 54. The signal processor analyzer 54 converts the output signals of the photomultiplier tube 54 into a signal which corresponds to a measure of radiation detected by the radiation detecting assembly 11a.

Preferably, the signal processor analyzer 54 comprises a Tennelec/Nucleus PCA-P spectroscopy software package which runs on a suitable personal computer (PC) system. The PCA-P software provides a complete NaI(Tl) or CsI(Tl) spectroscopy system. The spectral data are displayed on the display monitor 30.

A suitable personal computer (PC) system for the signal processor analyzer 30 includes at least 512K bytes of RAM memory and an MS DOS 3.0 (or higher) operating system. To provide color output, the PC system includes an EGA graphics display card and with the display monitor 30 being an EGA monitor. Alternately, a VGA graphics display card may be utilized with the monitor 30 being a VGA monitor.

The PCA-P software is resident on a half-length card which plugs in a single eight bit slot on the PC system motherboard. The PCA-P card includes a high voltage power supply, a charge-sensitive preamplifier, a shaping amplifier and a 1024 channel, 80 MHz Wilkinson Analog to Digital converter with single channel analyzer. The PCA-P card circuitry further includes built-in digital gain stabilization.

Although the invention has been described in its preferred form with a certain degree of particularity, it is understood that the present disclosure of the preferred form has been made only by way of example and that numerous changes in the details of construction, operation and combination and arrangement of parts may be resorted to without departing from the spirit and the scope of the invention as hereinafter claimed.

We claim:

1. An apparatus for measuring radiation at a region of interest inside a body, the apparatus comprising:

a) a catheter adapted to be inserted into a blood vessel, a length of the catheter sufficient to extend to the region of interest while a proximal end of the catheter remains outside the body;

b) a scintillation material supported by a distal portion of the catheter, the scintillation material generating pulses of radiation in response to being struck by rays of radiation, the scintillation material having proximal and distal ends spaced apart along a catheter extent;

c) a fiber optic light pipe attached to the catheter and coupled to the scintillation material for receiving pulses of radiation generated by the scintillation material and transmitting the pulses along a length of the light pipe, the fiber optic light pipe extending from the scintillation material to a region outside the body;

d) a radiation measuring assembly coupled to a portion of the fiber optic light pipe in the region outside the body for converting the pulses of radiation transmitted along the length of the fiber optic light pipe to a measure of radiation at the region of interest; and e) a first radiation blocking member positioned adjacent one of the proximal and distal ends of the scintillation material.

2. The apparatus for measuring radiation set forth in claim 1 wherein the catheter includes a lumen that extends through a portion of the catheter and wherein the scintillation material and a portion of the fiber optic light pipe are disposed in the lumen.

3. The apparatus for measuring radiation set forth in claim 1 wherein an index matching material is disposed between the scintillation material and an end of the fiber optic light pipe coupled to the scintillation material to facilitate receipt of the pulses of radiation by the fiber optic light pipe.

4. The apparatus for measuring radiation set forth in claim 1 additionally comprising a second radiation blocking member positioned adjacent an other of the distal and proximal ends of the scintillation material not bordered by said first radiation blocking member.

5. The apparatus for measuring radiation set forth in claim 1 wherein the scintillation material is a scintillation crystal comprising sodium iodide doped with thallium.

6. The apparatus for measuring radiation set forth in claim 1 wherein the catheter includes a guide member near a distal end of the catheter, the guide member including an aperture sized to slidingly overlie a guidewire such that the catheter may be routed along the guidewire to the region of interest.

7. The apparatus for measuring radiation set forth in claim 1 wherein the radiation measuring assembly includes a photodetector tube coupled to a proximal end of the fiber optic light pipe for converting the pulses of radiation traversing the light pipe into electric signals.

8. The apparatus for measuring radiation set forth in claim 7, wherein the radiation measuring assembly additionally includes a signal processor analyzer coupled to an output of the photodetector tube for converting the electric signals generated by the photodetector tube into the measure of radiation.

9. The radiation detection apparatus set forth in claim 1 wherein the scintillation material is a scintillation crystal comprising cesium iodide doped with thallium.

10. An apparatus for measuring radiation at a region of interest inside a body, the apparatus comprising:

a) a catheter adapted to be inserted into a blood vessel, a length of the catheter sufficient to extend to the region of interest while a proximal end of the catheter remains outside the body;

b) a scintillation material supported by a distal portion of the catheter, the scintillation material being a scintillation crystal consisting of sodium iodide doped with thallium and generating pulses of radiation in response to being struck by rays of radiation and wherein the scintillation crystal is generally cylindrical in shape having two end walls spaced apart by a side wall and further wherein a radiation blocking member is positioned adjacent one of the end walls;

c) a fiber optic light pipe attached to the catheter and coupled to the scintillation material for receiving pulses of radiation generated by the scintillation material and transmitting the pulses along a length of the light pipe, the fiber optic light pipe extending from the scintillation material to a region outside the body; and d) a radiation measuring assembly coupled to a portion of the fiber optic light pipe in the region outside the body for converting the pulses of radiation transmitted along the length of the fiber optic light pipe to a measure of radiation at the region of interest.

11. An apparatus for measuring radiation at a region of interest inside a body, the apparatus comprising:

a) a catheter adapted to be inserted into a blood vessel, a length of the catheter sufficient to extend to the region of interest while a proximal end of the catheter remains outside the body, the catheter being doped with light reflective particles;

b) a scintillation material supported by a distal portion of the catheter, the scintillation material generating pulses of radiation in response to being struck by rays of radiation;

c) a fiber optic light pipe attached to the catheter and coupled to the scintillation material for receiving pulses of radiation generated by the scintillation material and transmitting the pulses along a length of the light pipe, the fiber optic light pipe extending from the scintillation material to a region outside the body; and d) a radiation measuring assembly coupled to a portion of the fiber optic light pipe in the region outside the body for converting the pulses of radiation transmitted along the length of the fiber optic light pipe to a measure of radiation at the region of interest.

12. The apparatus for measuring radiation set forth in claim 11 wherein the catheter includes a lumen in which the fiber optic light pipe is disposed and a portion of the catheter adjacent the fiber optic light pipe is doped with light reflective particles.

13. A radiation detection apparatus comprising:

a) a catheter having a lumen supporting a fiber optic light pipe, the catheter adapted to be inserted into a body and having a length sufficient to permit a proximal end of the catheter to remain outside the body while a distal portion of the catheter is maneuvered within the body to a region of interest where radiation is sought to be detected and wherein at least a portion of a wall of the catheter is doped with a highly light reflective material;

b) a scintillation material disposed in the distal portion of the catheter and optically coupled to the fiber optic light pipe of the catheter, the scintillation material energized when stuck by photons emitted by a source of radiation to generate pulses of electromagnetic radiation which are transmitted to and traverse the fiber optic light pipe; and c) a radiation measuring assembly optically coupled to the fiber optic light pipe for sensing and converting the pulses of electromagnetic radiation traversing the fiber optic light pipe into a measure of radiation at the region of interest.

14. The radiation detection apparatus set forth in claim 13 wherein the light reflective material is comprised of $TiO_2$.

* * * * *